United States Patent
Palys

(10) Patent No.: US 8,507,758 B2
(45) Date of Patent: Aug. 13, 2013

(54) MARKERLESS TRANSFORMATION

(75) Inventor: Joseph Michael Palys, Davis, CA (US)

(73) Assignee: Seminis Vegetable Seeds, Inc., St. Louis, MO (US)

(*) Notice: Subject to any disclaimer, the term of this patent is extended or adjusted under 35 U.S.C. 154(b) by 0 days.

(21) Appl. No.: 13/335,646

(22) Filed: Dec. 22, 2011

(65) Prior Publication Data

US 2012/0096586 A1     Apr. 19, 2012

Related U.S. Application Data

(63) Continuation of application No. 10/794,798, filed on Mar. 5, 2004, now abandoned.

(60) Provisional application No. 60/452,850, filed on Mar. 7, 2003.

(51) Int. Cl.

| | |
|---|---|
| *C12N 15/82* | (2006.01) |
| *C12N 15/84* | (2006.01) |
| *C12N 15/10* | (2006.01) |
| *C12N 15/32* | (2006.01) |

(52) U.S. Cl.
CPC ........ *C12N 15/8265* (2013.01); *C12N 15/8201* (2013.01); *C12N 15/8205* (2013.01); *C12N 15/8209* (2013.01); *C12N 15/8286* (2013.01)
USPC ........... 800/302; 800/288; 800/294; 800/305; 800/306; 800/317.4; 435/6.11; 435/6.12; 435/7.1; 536/23.71

(58) Field of Classification Search
None
See application file for complete search history.

(56) References Cited

U.S. PATENT DOCUMENTS

| | | | |
|---|---|---|---|
| 5,164,310 A | 11/1992 | Smith et al. | |
| 5,225,341 A | 7/1993 | Yoder et al. | |
| 5,349,124 A | 9/1994 | Fischhoff et al. | |
| 5,919,999 A | 7/1999 | Ko et al. | |
| 5,994,624 A | 11/1999 | Trolinder et al. | |
| 6,218,188 B1 * | 4/2001 | Cardineau et al. | 435/468 |
| 2003/0115641 A1 | 6/2003 | Dobres et al. | |
| 2005/0097641 A1 | 5/2005 | Wolters et al. | |

FOREIGN PATENT DOCUMENTS

| | | |
|---|---|---|
| CA | 2087610 | 9/2000 |
| EP | 0 159 418 A1 | 10/1985 |
| EP | 0 429 093 B1 | 5/1991 |
| WO | WO 83/01176 A1 | 4/1983 |
| WO | WO 85/01856 A1 | 5/1985 |
| WO | WO 97/41228 A2 | 11/1997 |
| WO | WO 98/51806 A2 | 11/1998 |
| WO | WO 99/20776 A1 | 4/1999 |
| WO | WO 01/05936 A2 | 1/2001 |
| WO | WO 01/64023 A1 | 9/2001 |
| WO | 01/73084 | 10/2001 |
| WO | WO 01/81330 A2 | 11/2001 |
| WO | WO 02/055651 A2 | 7/2002 |
| WO | WO 03/009673 A1 | 2/2003 |
| WO | WO 03/010319 A2 | 2/2003 |
| WO | WO 03/048369 A2 | 6/2003 |
| WO | WO 2004/020636 A1 | 3/2004 |

OTHER PUBLICATIONS

Chupeau et al., "Recovery of Transgenic Trees after Electroporation of Poplar Protoplasts," *Transgenic Research*, 3:13-19 (1994), in parent U.S. Appl. No. 10/794,798.

Fraser et al., "Application of High-Performance Liquid Chromatography with Photodiode Array Detection to the Metabolic Profiling of Plant Isoprenoids," *The Plant Journal*, 24(4):551-558 (2000), in parent U.S. Appl. No. 10/794,798.

International Search Report issued in PCT/US04/06994 dated Nov. 23, 2005, herewith.

Jia et al., "Transformation of Tomato with the *BADH* Gene from *Atriplex* Improves Salt Tolerance," *Plant Cell Reports*, 21:141-146 (2002), in parent U.S. Appl. No. 10/794,798.

R. Ghorbel et al., "Green fluorescent protein as a screenable marker to increase the efficiency of generating transgenic woody fruit plants," *Theoretical and Applied Genetics* (1999) 99: 350-358, herewith.

Heidi F. Kaeppler et al., "Routine Utilization of Green Fluorescent Protein as a Visual Selectable Marker for Cereal Transformation," *In Vitro Cellular & Developmental Biology* (2001) 37: 120-126, herewith.

P. Vain et al., "The green fluorescent protein (GFP) as a vital screenable marker in rice transformation," *Theoretical and Applied Genetics* (1998) 96: 164-169, herewith.

* cited by examiner

*Primary Examiner* — David T Fox
(74) *Attorney, Agent, or Firm* — Thomas P. McBride; David R. Marsh; Arnold & Porter LLP

(57) ABSTRACT

Methods for identification of successful transformation without a need for in vitro selection are provided. Direct detection of nucleotide sequences of interest is described which eliminate the need for use of ancillary nucleotide sequences.

18 Claims, No Drawings

MARKERLESS TRANSFORMATION

CROSS REFERENCE

This application is a continuation of U.S. application Ser. No. 10/794,798 filed Mar. 5, 2004, now Abandoned, which claims priority and is related to U.S. Provisional Patent Application No. 60/452,850 filed Mar. 7, 2003.

BACKGROUND OF THE INVENTION

This invention relates to improved methods for the identification of transformed plants. More specifically, it relates to a method which eliminates the need for use of ancillary nucleotide sequences, such as selectable markers, to identify successful transformation by providing a method for direct detection of the expression of nucleotide sequences of interest in regenerated plant tissue.

The publications, patents and other materials used herein to illuminate the background of the invention, and in particular cases, to provide additional details respecting the practice, are incorporated by reference, and for convenience are referenced in the following text by author and date.

Early transformation procedures resulted in very low frequency of transformation, where only about one out of every one million plant cells were transformed successfully. This very low frequency of transformation presented a problem in identifying the single cell that had been transformed among all of the cells that were not transformed. This identification problem has been addressed generally by physically linking ancillary nucleotide sequences, such as a bacterial gene that confers antibiotic resistance, to the gene of interest. This construct is then used to transform a culture of plant cells or protoplasts, and the linked gene for antibiotic resistance can be used as a selectable marker to identify successful transformation with the gene of interest. Cells that have been transformed with the gene of interest can be easily identified because the only plant cells able to survive are the plant cells containing the resistance gene (and linked gene of interest).

The presence of ancillary marker sequences, such as antibiotic resistance genes, have provided a practical solution to the task of identifying successful transformation events. However, these ancillary sequences do not positively contribute to the final cultivar and, in fact, they lessen its commercial desirability. The environmental and biological effects of the presence of this unwanted genetic material in the cultivar is unclear, and commercialization of transgenic plants has met resistance and skepticism in large part because of the uncertainty associated with the marker material sequences. The presence of these undesirable sequences may also complicate the regulatory procedures necessary to bring the cultivar to the marketplace. Thus, it would be desirable to devise an alternative method of identifying successful transformation events which is not based on the use of bacterial resistance genes or other ancillary sequences which remain in the cultivar.

Known methods for eliminating marker, or other ancillary, sequences from the transformed cultivar include the use of transposons. In this method, plants are first transformed by use of transposons, which include marker genes. The gene of interest is either included within a transposon or, alternatively, in a DNA construct which is not part of the transposon. Subsequent crosses are required in order to eliminate the marker sequences by selecting progeny in which they do not appear (U.S. Pat. No. 5,225,341, Yoder et al.; issued Jul. 6, 1993). Additional disadvantages of the use of markers include the need to segregate away the marker DNA and the DNA footprint that the transposon leaves in the plant genomic DNA upon excising. Although the marker sequences are not present in the mature plant, this method is also based on the use of marker sequences and requires culturing on selective medium as a method for identifying transformed plant cells prior to regeneration of the plant.

A reliable method for selection of transformed plants which does not require the use of transposons, insertion of ancillary marker sequences or culturing on selective media, would simplify the transformation process, increase public acceptance and avoid related regulatory problems.

SUMMARY OF THE INVENTION

The invention relates to a method for producing a transgenic plant that includes a nucleotide sequence of interest and is free of ancillary nucleic acid sequences, where said method comprises: (a) transforming a plant tissue or plant cell with a gene of interest; (b) regenerating said transformed plant tissue or plant cell to produce a new plant; and (c) directly detecting the presence or absence in said regenerated plant of the nucleotide sequence, or encoded product of said nucleotide sequence, of interest. The direct detection may be southern hybridization, polymerase chain reaction, western hybridization for the gene product of interest and HPLC for metabolic product of the protein product.

The invention also relates to plants transformed by the described method and the seed and progeny produced by the transformed plants.

DETAILED DESCRIPTION

Definitions

In order to provide an understanding of several of the terms used in the specification and claims, the following definitions are provided:

"Ancillary nucleotide sequences" refers to nucleic acid sequences other than the nucleotide sequences of interest. Examples of ancillary nucleotide sequences are selectable marker sequences, which provide resistance to antibiotics, reporter sequences, or combinations thereof.

"Direct detection" of presence or absence of a gene or gene product of interest in a regenerated plant refers to a method or process allowing the detection of the presence of a gene or gene product of interest directly from a regenerated plant.

"Gene" refers to a DNA sequence that encodes a recoverable bioactive polypeptide or precursor. The polypeptide can be encoded by a full-length gene sequence or any portion of the coding sequence so long as the enzyme activity is maintained.

"Gene of interest" and "nucleotide sequence of interest" refers to a recombinant nucleic acid that will produce the desired plant phenotype of interest.

"Gene product of interest" and "encoded product of nucleotide sequence of interest" refers to the polypeptide produced by the gene of interest and nucleotide sequence of interest, respectively.

"Encode" refers to a polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"In vitro preferential growth conditions" refers to the process of in vitro selection.

"In vitro selection" refers to the process in which regenerating plant cells containing a gene of interest (and linked to a marker sequence) are exposed to a treatment that preferentially allows or prevents the growth of cells containing the marker sequence.

"Marker sequence" and "selectable marker" refer to DNA encoding for a gene that can be used for in vitro selection.

"Markerless identification" refers to the process in which transformed plants are produced without in vitro selection or use of ancillary nucleotide sequences, and transformation is confirmed by direct detection of the gene or gene product of interest.

To "regenerate plants" refers to the process of producing a new plant from a plant cell or plant tissue.

"Recombinant nucleic acid" refers to a nucleic acid that is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

EXAMPLES

The present invention is described by reference to the following Examples, which are offered by way of illustration and are not intended to limit the invention in any manner. Standard techniques well known in the art or the techniques specifically described below were utilized.

Example 1

Production of Transformants of Tomato without In Vitro Selection

Tomato seeds (T57) were surface sterilized in a 20% solution of commercial bleach (stock containing 5.25% sodium hypochlorite) for 20 minutes under constant stirring. Several drops of Tween 20 were added to the sterilization mix as a wetting agent. Seeds were rinsed 3 times in sterile distilled water, blotted dry with sterile filter paper and then transferred to Sigma P4928 phytacons containing 80 ml of MS medium (25 seeds per phytacon).

Sterilized seeds were germinated in Sigma P4928 phytacons in a growth room at 24° C. with a 16 hour photoperiod. Seedlings were grown for 8 days before explanting. Explanting plates were prepared by placing a Whatman No. 2, 9 cm filter disc onto the agar surface of a 100 mm×25 mm petri dish containing 25 ml of RIF medium. Tomato seedlings were decapitated and placed into a 100 mm×25 mm petri dish containing sterile filter paper wetted with sterile, distilled water. Explants were prepared by cutting each cotyledon into 3 pieces. The 2 proximal pieces were transferred onto the explanting plate, the distal section was discarded. One hundred twenty cotyledonary explants were placed on each explanting plate. Twenty explanting plates and one control plate were prepared. Both explants and control were cultured in the dark at 24° C. for 24 hours.

Two sequential 20 ml overnight liquid *Agrobacterium* (pJG2004) cultures were grown. The bacteria contained a binary vector with a mosaic virus (FMV) promoter driving a hybrid Cry1Ac-1Acf Bt protein and no selectable marker. The first culture was grown in 523 medium with the following antibiotics to select *Agrobacterium* cells containing the binary vector: Kanamycin 50 mg/L, Spectinomycin 100 mg/L, and Streptomycin 100 mg/L. The second overnight culture was initiated with 1 ml of the first overnight culture and was grown in AB minimal medium with the following antibiotics: Kanamycin 50 mg/L, Spectinomycin 100 mg/L, and Streptomycin 100 mg/L. Cultures were grown at 28° C. with constant shaking on a gyratory shaker. The second overnight culture was centrifuged in 38 ml sterile oakridge tubes for 5 minutes at 8000 rpm in a Beckman JA20 rotor. The pellet was resuspended in 10 ml of liquid MS medium plus acetosyringone at 600 µM. The concentration was adjusted to an OD of 0.75 at 600 nM, by diluting with liquid MS plus 600 µM acetosyringone.

Seven milliliters of the *Agrobacterium* suspension (0.75 OD) were aliquoted onto each of 19 explanting plates. Cocultivation was allowed to proceed for 20 minutes at which time the *Agrobacterium* suspension was aspirated off and the explants blotted dry with sterile filter paper discs. The plates were sealed with parafilm and incubated in the dark at 24° C. for 48 hours.

After co-cultivation, all explants were transferred and allowed to regenerate, without selection, on 100 mm×25 mm petri plates (20 explants per plate) containing 25 ml of R1T medium. After 14 days, the explants were transferred to fresh R1/2T medium. After 14 days, the regenerating tissues at the edge of the explants were excised away from the primary explant and were transferred onto fresh RZ1/2C medium. Alternatively, the primary explants can be transferred onto fresh RZ1/2C medium. After two weeks, regenerating tissues were transferred again to fresh RZ1/2C medium. Regenerating tissues were subsequently rotated between ROC media and RZ1/2C media at 2 week intervals. As well-defined shoots arose, they were excised and transferred to ROC medium for rooting.

Identification of Transformants.

The rooted in vitro (grown on medium) shoots were analyzed to identify transformants. Small pieces of leaves were removed from the in vitro regenerated putative transformants. For purposes of this experiment, 5 to 10 samples were pooled together in a 10 ml tube, and ground with a Ultraturrax T25 homogenizer at 25,500 rpm in 0.5 ml of 0.1 M Borate buffer (sodium borate (tetra) decahydrate 38.142 g/L; Tween 20, 5 ml/L; pH 7.5). The number of samples in a pool can be varied, based on the sensitivity of the detection means and the ability to effectively grind the tissue in a small volume of buffer. Once ground, a GenecheckJ BT dipstick (SDI, Inc.) was placed in the tube containing the leaf tissue homogenate. After 2 hours, the dipstick was read. A positive reaction indicated the presence of Bt protein and, therefore, identified successful transformation within the pooled samples. Alternatively, the presence of the Bt protein can be identified using conventional assay techniques such as antigen/antibody binding or PCR. With other techniques, larger numbers of samples may be pooled.

For pools which tested positive, individual leaflet samples were taken from each of the 5 to 10 putative transformants that made up the pooled sample. These were ground separately and tested individually with the BT dipstick in the same manner as with the pooled samples. Individual shoots that tested positive were subsequently transplanted to soil.

Confirmation of Identification.

After 2 weeks growth in soil, in vitro *Spodoptera exiqua* feeding screens were performed to confirm successful transformation. T0 lines that tested positive for the presence of the Bt proteins were subsequently tested for insect resistance.

Replicate leaf disc samples were taken from the Bt positive T0 lines and placed into wells of a Falcon 28 well plate containing 1 ml of 2% water agar. Four *Spodoptera* larvae were added to each leaf disc sample. Non-transformed T57 leaf discs were included as a control. Plates were sealed with perforated film and incubated at 28° C. for 4 days. Feeding damage was rated using a 7 point qualitative scale, with the following ratings: 0=no damage; 1=1-10% damage; 2=11-20% damage; 3=21-30% damage; 4=31-40% damage; 5=41-50% damage; 6=51-100% damage. Resistant T0 plants were grown to maturity in a greenhouse and the screen was repeated on individual plants from T1 segregating populations derived from the T0 lines.

Three T0 lines, 996081-49A-4, 996081-91B-7, and 996081-46B-7A and 996081-46B-7A (2 clonal lines of the same event) yielded a positive BT dipstick reaction, indicating that they were transgenic. In vitro insect screens for these T0 lines indicated resistance to *Spodoptera exiqua* larvae. This reconfirmed that they were transgenic. All lines showed stable integration of the Bt transgene based on BT dipstick analysis of T1 progeny, with segregation ratios (+BT:−BT) of 32:11, 27:8, 42:13, and 43:10, respectively.

TABLE 1

Media Composition (g(mg)/L.)

|  | MS | R1 | R1T | R1/2T | RZ1/2C | ROC |
|---|---|---|---|---|---|---|
| Gibco MS Salts | 4.3 g | 4.3 g | 4.3 g | 4.3 g | 4.3 g | 4.3 g |
| RO Vitamins (100×) | 10 ml | — | — | 5 ml | 5 ml | 10 ml |
| R1 Vitamins (100×) | — | 10 ml | 10 ml | 10 ml | — | — |
| RZ Vitamins (100×) | — | — | — | — | 5 ml | — |
| Glucose | 16 g | 16 g | 16 g | 16 g | 16 g | 16 g |
| Timentin | — | — | 100 mg | 100 mg | — | — |
| Carbenicillin | — | — | — | 400 mg | 400 mg | 400 mg |
| Noble Agar | 9.0 g | 9.0 g | 9.0 g | 9.0 g | 9.0 g | 9.0 g |
| MES | — | — | — | 600 mg | 600 mg | 600 mg |
| pH | 5.7 | 5.7 | 5.7 | 5.7 | 5.7 | 5.7 |

RO Vitamins (100×)
♂ Nicotinic acid 500 mg/L
Thiamine HCL 50 mg/L
Pyridoxine HCL 50 mg/L
Myo-inositol 10.0 g/L
Glycine 200 mg/L
pH 5.7
Filter sterilize, adding after autoclaving.
R1 Vitamins: RO Vitamins plus Zeatin (0.65 mg/L) and IAA (1.0 mg/L)
RZ Vitamins: RZ Vitamins plus Zeatin (0.65 mg/L)

TABLE 2

523 Medium Composition

| Sucrose | 10 g/L |
| Casein Enzymatic Hydrolysate | 8 g/L |
| Yeast Extract | 4 g/L |
| $K_2HPO_4$ | 2 g/L |
| $MgSO_4 \cdot 7H_2O$ | 0.3 g/L | pH 7.0
AB Medium

| Part A | | Part B (10 × Stock) | |
|---|---|---|---|
| $K_2HPO_4$ | 3 g/L | $MgSO_2 \cdot 7H_2O$ | 3 g/L |
| $NaH_2PO_4$ | 1 g/L | CaCl2 | 0.1 g/L |
| $NH_4Cl$ | 1 g/L | $FeSO_4 \cdot 7H_2O$ | 0.025 g/L |
| Prepare at 0.9 × volume | | Glucose | 50 g/L |

Mix 900 ml Part A with 100 ml Part B

Example 2

Production of Transformants of Lettuce without In Vitro Selection

Seeds of lettuce variety "Conquistidor" were surface sterilized for 20 minutes in 20% commercial bleach solution (5.25% sodium hypochlorite). Disinfection is followed by three, 50 ml rinses with sterile, distilled water. Seeds are germinated in Sigma P1552 Phytatrays containing 100 ml of ½× Hoagland's media supplemented with 10 mg/L Giberillic acid, solidified with 8 gm/L Gibco tissue culture grade agar. Cultures are incubated at 25° C. with a 16-hour photoperiod for six to seven days.

The *Agrobacterium* culture is prepared by inoculating 10 ml of liquid MG/L medium with 100 µl frozen bacterial suspension of pJG2004, containing a binary vector with a FMV promoter driving a hybrid Cry1Ac-1AcfBt protein and no selectable marker. The liquid culture is incubated on a gyratory shaker at 28° C. for 24 hours. Five ml of the overnight are then diluted with 15 ml of TY AS medium. This is then returned to the shaker for 24 hours. Cotyledons are aseptically removed and cut at both the base and the tip and soaked in the *Agrobacterium* broth culture ($OD_{600}$ 0.1) for a maximum of 15 minutes. The cotyledon explants are then plated in petri plates containing 20 ml of MSO-C co-culture medium. Plates are incubated at 23° C. with a 16 hour photoperiod. After 48 to 72 hours, cotyledon pieces are transferred onto plates containing 20 ml of MSO-I induction medium. Plates are incubated at 23° C. for seven days and then transferred to fresh MSO-I. After three to four weeks, shoots begin to develop on the cotyledon pieces. These are removed and plated on 20 ml MSO-E elongation medium. After elongation, shoots are transferred to "phytatrays" or 150×25 mm culture tubes containing MSO-SE. After six to eight weeks, the developed shoots are transferred to 150×25 mm culture tubes containing 20 ml MSO-R rooting medium. After 7 to 10 days of incubation at 23° C. and 16 hour photoperiod, roots will develop and the shoot is transferred to soil.

Small leaflets were sampled from the in vitro regenerated putative transgenics. Five to 12 samples were pooled together in a 10 ml tube and ground with a Ultraturrax T25 homogenizer at 25,500 rpm in 0.5 ml of 0.1 M Borate buffer. Once ground, a Genecheck™ BT dipstick was placed in the tube containing the leaf tissue homogenate. After 1 to 2 hours, the dipstick was read. A positive reaction indicated the presence of Bt protein from a transgenic plant. If a positive reaction occurred, individual leaf samples were retaken from each of the putative transgenics that made up the pooled sample, ground separately and tested individually with the BT dipstick in the same manner as with the pooled samples.

T0 lines that tested positive for the presence of the Bt proteins were subsequently tested for insect resistance as follows: Replicated leaf disc samples were taken from the Bt positive lines and placed into wells of a Falcon 28 well plate containing 0.5 ml of 0.8% water agar. Four *Spodoptera exiqua* larvae were added to each leaf disc sample. Non-transformed leaf discs were included as a control. Plates were sealed with perforated film and incubated at 28° C. for 4 days. Feeding damage was rated using a 5 point qualitative scale (Ratings: 0=no damage, 1=less than 10% damage, 2=10-30% damage, 3=31-50% damage, 4=greater than 50% damage).

A total of 141 regenerated putative transgenics were sampled and analyzed. Three lines, 001339-007, 001339-008, and 001339-010, yielded a positive dipstick reaction, indicating the presence of the Bt protein. All three lines were resistant to *Spodoptera exiqua* larvae, with average feeding damage ratings of 0, 1.5, and 0, respectively. These lines were transferred to the greenhouse and T1 seed produced.

Three T1 seeds of each line were planted. Individual leaf samples were ground in a 10 ml tube, with an Ultraturrax T25 homogenizer at 25,500 rpm in 0.5 ml of 0.1 M Borate buffer. Once ground, a Genecheck™ BT dipstick was placed in the tube containing the leaf tissue homogenate. After 1 to 2 hours, the dipstick was read. A positive reaction indicated the presence of Bt protein from a transgenic plant. A positive dipstick reaction was observed within the T1 progeny of 001339-007, 001339-008, and 001339-010, indicating the stable integration of the Bt gene in these lines.

TABLE 3

| Media | | | | |
|---|---|---|---|---|
| | MSO-C | MSO-I | MSO-SE | MSO-R |
| Murashige's Minimal Organics Media Gibco | 34.6 g | 34.6 g | 34.6 g | 34.6 g |
| Naphthalene Acetic Acid | 0.1 mg | 0.1 mg | 0.05 mg | |
| Benzylaminopurine | 0.1 mg | 0.1 mg | 0.01 mg | |
| Carbenicillin | | 500 mg | 500 mg | |
| Acetosyringone | 40 mg | | | |
| Agar Gibco Tissue Culture Grade | 8 g | 8 g | 8 g | 8 g |
| pH | 5.7 | 5.7 | 5.7 | 5.7 |

(all ingredients are amount per liter)

TABLE 4

| MG/L (Mannitol-Glutamate/Luria) Medium | |
|---|---|
| LB broth, Miller (Difco # 044-017-3) | 12.5 g/L |
| Mannitol | 5.0 g/L |
| Monosodium glutamate (glutamic acid) | 1.16 g/L |
| $KH_2PO_4$ | 0.25 g/L |
| $MgSO_4$ | 0.1 g/L |
| Biotin | 1.0 mg/L |
| pH to 7.0 | |

TABLE 5

| TY AS Medium | |
|---|---|
| Tryptone | 5 g/L |
| Yeast Extract | 3 g/L |
| Acetosyringone (2 mg/ml stock) | 20 ml/L |
| pH to 5.5 | |

TABLE 6

| Borate Buffer 0.1M | |
|---|---|
| Sodium Borate (tetra) decahydrate | 38.142 g/L |
| Tween 20 | 5 ml/L |
| pH to 7.5 | |

Example 3

Production of Transformants of Cabbage without In Vitro Selection

Seeds of cabbage variety "CFO4R" were surface sterilized in a 15% solution of commercial bleach (stock containing 5.25% sodium hypochlorite) for 20 minutes under constant stirring. Several drops of Tween 20 were added to the sterilization mix as a wetting agent. Seeds were rinsed 3 times in sterile distilled water, blotted dry with sterile filter paper and then transferred to 100 mm×25 mm petri dishes containing 25 ml of ¼×MS medium. Sterilized seeds were germinated in the dark at 24° C. for 2 days, followed by 7 days in the light with a 16 hour photoperiod.

Pre-culture was performed two days prior to inoculation. Petioles are explanted at the point of attachment with the hypocotyls. The cotyledons are separated and as much of the axis tissue as possible is removed. The base of the petiole is inserted into 25 ml of N.1 B3 0/0 medium in a 100 mm×25 mm petri dish and incubated in the light.

*Agrobacterium* culture and preparation was performed by growing two sequential 20 ml overnight liquid cultures of pJG1002, containing a binary vector with a 35S promoter driving Cry1Bb Bt protein, an eFMV promoter driving Cry1Ac Bt protein and no selectable marker. The first culture was grown in MG/L medium with the following antibiotics: Kanamycin 50 mg/L, Spectinomycin 100 mg/L, and Streptomycin 100 mg/L. The second overnight culture was initiated with 5 ml of the first overnight culture and was grown in TY AS medium with the following antibiotics: Kanamycin 50 mg/L, Spectinomycin 100 mg/L, and Streptomycin 100 mg/L. Cultures were grown at 28° C. with constant shaking on a gyratory shaker. The second overnight was centrifuged in 38 ml sterile oakridge tubes for 5 minutes at 8500 rpm in a Beckman JA20 rotor. The pellet was resuspended in liquid MS medium plus acetosyringone at 500 μM, and diluted to 0.5 OD at 600 nm.

Co-cultivation was performed with explants which were inoculated by submersing the cotyledons, with the base down, in the *Agrobacterium* suspension for 15 minutes. The bacterial solution is removed and the cotyledons are placed, with the base down, on 25 ml of N.1 B3 0/0 medium in a 25×100 mm Petri dish, overlaid with 2 ml of tobacco suspension cells and a Whatman No. 2, 9 cm filter disc. The tobacco suspension is maintained on MS medium supplemented with 0.5 mg/L 2,4-D on a rotary shaker. The plates are co-cultivated for 3 days in the dark.

Regeneration was performed after 3 days of co-cultivation. Explants were transferred to 100 mm×25 mm petri plates containing 25 ml of N.1 B3 0/500 medium. Every 14 days, explants were transferred to fresh N 0.1 B3 0/500 medium. After 33 days, the explants were transferred to 100 mm×25 mm petri plates containing 25 ml of IBA.5 0/500 elongation medium. As well-defined shoots arose, they were excised and transferred to IBA 0.5 0/500 medium for rooting.

Shoot analysis was performed on samples of small leaf pieces from the in vitro regenerated putative transgenics. Ten samples were pooled together in a 10 ml tube and ground with a Ultraturrax T25 homogenizer at 25,500 rpm in 0.5 ml of 0.1 M Borate buffer. Once ground, a Genecheck™ BT dipstick was placed in the tube containing the leaf tissue homogenate. After 2 hours, the dipstick was read. A positive reaction indicated the presence of Bt protein from a transgenic plant. If a positive reaction occurred, individual leaf samples were retaken from each of the 10 putative transgenics that made up the pooled sample, ground separately and tested individually with the BT dipstick in the same manner as with the pooled samples. Individual plants that tested positive were subsequently transplanted to soil.

Eighteen T0 lines yielded a positive BT dipstick reaction. Transformations were confirmed via Southern Hybridization analysis. Genomic DNA was isolated from one sample from each event using the mini urea prep protocol. Two, 7.5 μg aliquots were digested for each sample, one with HindIII and one with XbaI. Digested DNAs were run on a gel and blotted onto nylon membrane. The HindIII blot was probed with Cry1Bb and the XbaI blot with Cry1Ac. The data indicated that all 12 lines were transformed.

TABLE 7

Media Composition

|  | MS | N.1 B3 0/0 | N.1 B3 0/500 | IBA .5 0/500 |
|---|---|---|---|---|
| Gibco MS Salts | 4.3 g | 4.3 g | 4.3 g | 4.3 g |
| Sucrose | 30 g | 30 g | 30 g | 30 g |
| LNS Vitamins (1000 × Stock) | 1 ml | 1 ml | 1 ml | 1 ml |
| Carbenicillin | — | — | 500 mg | 500 mg |
| Myo-inositol | 100 mg | 100 mg | 100 mg | 100 mg |
| Naphthalene Acetic Acid | — | 0.1 mg | 0.1 mg | — |
| Benzylaminopurine | — | 3.0 mg | 3.0 mg | — |
| Indobutryic Acid | — | — | — | 0.5 mg |
| pH | 5.8 | 5.8 | 5.8 | 5.8 |
| Agar (Gibco Tissue Culture Grade) | 7.0 g | 7.0 g | 7.0 g | 7.0 g |

All ingredients are amount per liter

TABLE 8

LNS Vitamins 1000 × Stock

| Nicotinic Acid | 0.05 g/l |
|---|---|
| Thiamine | 0.01 g/l |
| Pyridoxine | 0.05 g/l |
| Glycine | 0.20 g/l |

TABLE 9

MG/L (Mannitol-Glutamate/Luria) Medium

| LB Broth, Miller (Difco # 044-017-3) | 12.5 g/L |
|---|---|
| Mannitol | 5.0 g/L |
| Monosodium glutamate (glutamic acid) | 1.16 g/L |
| KH$_2$PO$_4$ | 0.25 g/L |
| MgSO$_4$ | 0.1 g/L |
| Biotin | 1.0 mg/L |
| pH to 7.0 | |

TABLE 10

TY AS Medium

| Tryptone | 5 g/L |
|---|---|
| Yeast Extract | 3 g/L |
| Acetosyringone (2 mg/ml stock) | 20 ml/L |
| pH to 5.5 | |

TABLE 11

Borate Buffer 0.1M

| Sodium Borate (tetra) decahydrate | 38.142 g/L |
|---|---|
| Tween 20 | 5 ml/L |
| pH to 7.5 | |

It will be appreciated that the methods and compositions of the instant invention can be incorporated in the form of a variety of embodiments, only a few of which are disclosed herein. It will be apparent to the artisan that other embodiments exist and do not depart from the spirit of the invention.

Thus, the described embodiments are illustrative and should not be construed as restrictive.

I claim:

1. A method for producing a transgenic plant comprising a nucleotide sequence of interest inserted into its genome, where said method consists essentially of:
   a) transforming a plant tissue or plant cell with said nucleotide sequence of interest, which nucleotide sequence of interest comprises a gene of interest; wherein said plant tissue or plant cell is not transformed with an ancillary nucleotide sequence comprising a reporter sequence or a selectable marker sequence;
   b) regenerating said plant tissue or plant cell without selection for a reporter or selectable marker following said transforming, to produce a transgenic plant; and
   c) directly detecting the presence or absence in said transgenic plant of said nucleotide sequence of interest, an encoded product of said nucleotide sequence of interest, or a metabolic product of said encoded product;
   wherein said transgenic plant comprises said nucleotide sequence of interest introduced by said transforming;
   wherein said transforming does not introduce a transposable element into said plant tissue or plant cell; and
   wherein said nucleotide sequence of interest encodes one or more products selected from the group consisting of a hybrid Cry1Ac-1Acf *Bacillus thuringiensis* (Bt) protein, a Cry1Bb Bt protein, and a Cry1Ac Bt protein.

2. The method of claim 1, wherein directly detecting comprises the use of a method selected from the group consisting of southern hybridization, polymerase chain reaction, and western hybridization for the nucleotide sequence or encoded product; and HPLC for a metabolic product of the encoded product.

3. The method of claim 2, wherein directly detecting comprises the use of a method selected from the group consisting of southern hybridization for the nucleotide sequence of interest and HPLC for a metabolic product of the encoded product.

4. The method of claim 2, wherein directly detecting comprises the use of a method selected from the group consisting of polymerase chain reaction for the nucleotide sequence of interest and HPLC for a metabolic product of the encoded product.

5. The method of claim 2, wherein directly detecting comprises the use of a method selected from the group consisting of western hybridization for the encoded product and HPLC for a metabolic product of the encoded product.

6. The method of claim 1, wherein directly detecting comprises the use of antibody binding to the encoded product or HPLC for a metabolic product of the encoded product.

7. The method of claim 1, wherein said directly detecting comprises pooling samples from a group of plants.

8. The method of claim 1, wherein said transgenic plant is selected from the group consisting of tomato, lettuce, and cabbage.

9. The method of claim 1, wherein said plant tissue or plant cell is from a cotyledon explant.

10. A method for producing a transgenic plant comprising a nucleotide sequence of interest inserted into its genome, where said method comprises:
   a) transforming a plant tissue or plant cell with said nucleotide sequence of interest, which nucleotide sequence of interest comprises a gene of interest; wherein said plant tissue or plant cell is not transformed with an ancillary nucleotide sequence comprising a reporter sequence or a selectable marker sequence;
   b) regenerating said plant tissue or plant cell without screening for said nucleotide sequence of interest, an encoded product of said nucleotide sequence of interest, or a metabolic product of said encoded product; and without selection for a reporter or selectable marker following said transforming, to produce a transgenic plant; and c) directly detecting the presence or absence in said transgenic plant of said nucleotide sequence of interest, said encoded product of said nucleotide sequence of interest, or said metabolic product of said encoded product;

wherein said transgenic plant comprises said nucleotide sequence of interest introduced by said transforming; and wherein said nucleotide sequence of interest encodes one or more products selected from the group consisting of a hybrid Cry1Ac-1Acf *Bacillus thuringiensis* (Bt) protein, a Cry1Bb Bt protein, and a Cry1Ac Bt protein.

11. The method of claim 10, wherein said transforming does not introduce a transposable element into said plant tissue or plant cell.

12. The method of claim 10, wherein directly detecting comprises the use of a method selected from the group consisting of southern hybridization, polymerase chain reaction, and western hybridization for the nucleotide sequence or encoded product; and HPLC for a metabolic product of the encoded product.

13. The method of claim 10, wherein directly detecting comprises the use of antibody binding to the encoded product or HPLC for a metabolic product of the encoded product.

14. The method of claim 10, wherein said directly detecting comprises pooling samples from a group of plants.

15. The method of claim 10, wherein said transgenic plant is selected from the group consisting of tomato, lettuce, and cabbage.

16. The method of claim 10, wherein said plant tissue or plant cell is from a cotyledon explant.

17. The method of claim 1, wherein said transforming involves *Agrobacterium*.

18. The method of claim 10, wherein said transforming involves *Agrobacterium*.

* * * * *